(12) United States Patent
Furuki et al.

(10) Patent No.: US 8,211,380 B2
(45) Date of Patent: Jul. 3, 2012

(54) BIO-ASSAY SUBSTRATE, BIO-ASSAY APPARATUS, AND READING APPARATUS

(75) Inventors: Motohiro Furuki, Shinagawa-Ku (JP); Hisayuki Yamatsu, Shinagawa-Ku (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 12/888,102

(22) Filed: Sep. 22, 2010

(65) Prior Publication Data

US 2011/0008879 A1    Jan. 13, 2011

Related U.S. Application Data

(62) Division of application No. 10/477,587, filed as application No. PCT/JP03/03089 on Mar. 14, 2003, now abandoned.

(30) Foreign Application Priority Data

Mar. 15, 2002    (JP) ................... 2002-071984

(51) Int. Cl.
     *G01N 33/00*    (2006.01)
(52) U.S. Cl. ....... 422/403; 422/400; 422/401; 422/68.1; 422/415
(58) Field of Classification Search ............... 422/403, 422/400, 401, 68.1, 415
See application file for complete search history.

(56) References Cited

U.S. PATENT DOCUMENTS

| | | | |
|---|---|---|---|
| 5,892,740 A | 4/1999 | Nagasawa et al. | |
| 5,922,617 A | 7/1999 | Wang et al. | |
| 6,172,952 B1 | 1/2001 | Inokuchi et al. | |
| 6,312,901 B2 | 11/2001 | Virtanen | |
| 6,602,702 B1 | 8/2003 | McDevitt et al. | |
| 7,014,815 B1 * | 3/2006 | Worthington et al. | 422/82.05 |

FOREIGN PATENT DOCUMENTS

| | | |
|---|---|---|
| EP | 0417305 | 3/1991 |
| JP | 9-231699 | 9/1997 |
| JP | 11-075812 | 3/1999 |
| JP | 11-094747 | 4/1999 |
| JP | 2000-346842 | 12/2000 |
| JP | 2001-238674 | 9/2001 |
| JP | 2002-014106 | 1/2002 |
| JP | 2002-040036 | 2/2002 |

(Continued)

OTHER PUBLICATIONS

Office Action issued from the Japanese Patent Office on Sep. 2, 2008, in counterpart Japanese application No. 2003-068481, 2 pages.

(Continued)

*Primary Examiner* — Sam P Siefke
(74) *Attorney, Agent, or Firm* — Finnegan, Henderson, Farabow, Garrett & Dunner, L.L.P.

(57) ABSTRACT

A bioassay substrate high in integration amount, free in grouping of substances, low in cost, and the like are provided. Specifically, a bioassay substrate includes detection surfaces S on which detection substances can be solidified, the detection surfaces S is provided on a surface of a disk form substrate capable of reading out record information optically, and the detection surfaces S is provided in groove structures (pits) provided in the surface of the substrate radially as viewed on the upper side at predetermined intervals. A bioassay system using the bioassay substrate and a readout system are also provided.

12 Claims, 6 Drawing Sheets

| | FOREIGN PATENT DOCUMENTS | |
|---|---|---|
| JP | 2002-065274 | 3/2002 |
| JP | 2002-250726 | 9/2002 |
| WO | WO-98/01533 | 1/1998 |
| WO | WO-99/24822 | 5/1999 |
| WO | WO-99/26059 | 5/1999 |
| WO | WO-99/35499 | 7/1999 |
| WO | WO-02/06836 | 1/2002 |

OTHER PUBLICATIONS

International Search Report of PCT/JP03/03089, mailed Apr. 30, 2003, 4 pages.

* cited by examiner

BIO-ASSAY SUBSTRATE, BIO-ASSAY APPARATUS, AND READING APPARATUS

CROSS REFERENCE TO RELATED APPLICATIONS

This application is a divisional of U.S. patent application Ser. No. 10/477,587, filed Nov. 13, 2003 (pending), which is a 371 national phase entry of PCT/JP03/03089, filed Mar. 14, 2003, which claims priority to Japanese Patent Application No. JP 2002-71984, filed Mar. 15, 2002, all of which are incorporated herein by reference.

TECHNICAL FIELD

The present invention relates to a disk form information recording medium, which constitutes a bioassay tool useful in the bioinformatics field and the like. More particularly, the present invention relates to a bioassay substrate so designed that hybridization or other intermolecular reaction is effected with high precision by spotting a solution containing labeled target substance to substrate surface sites where detection substances are solidified, a bioassay method using the substrate, a bioassay system utilizing the substrate, and a record information readout system.

BACKGROUND ART

The conventional technologies to which the present invention pertains will be described below. At present, integrated substrates for bioassay, which are called DNA chips or DNA microarrays (hereinafter generically referred to as "DNA chips") and on which predetermined DNAs are microarrayed by a microarraying technology, have been utilized for gene mutation analysis, SNPs (monobasic polymorphism) analysis, gene expression frequency analysis, etc., and have come to be used in a wide range of fields including novel medicament development, clinical diagnosis, pharmacogenomics, forensic medicine, etc.

The DNA chip is said to have the characteristic feature that it enables comprehensive analysis of intermolecular reactions such as hybridization since a plurality of kinds of and a multiplicity of DNA oligochains, cDNAs (complementary DNAs), or the like are integrated on a glass substrate or silicon substrate.

An example of the analytical technique using a DNA chip will be described. In the analytical technique, using DNA probes solidified on a glass substrate or silicon substrate, an mRNA extracted from a cell, a tissue, or the like is subjected to PCR amplification while incorporating a fluorescent probe dNTP by a reverse transcription PCR reaction or the like; hybridization is conducted on the substrate; and fluorometry is carried out by use of a predetermined detector.

Here, the DNA chips are classified into two types. A first type is the type in which oligonucleotide is synthesized directly on a predetermined substrate by use of a photolithographic technique applying the semiconductor exposure technique. A representative chip of this type is the chip produced by Affymetrix. This type of DNA chips are high in the degree of integration, but is limited as to the DNA synthesis on the substrate; the length of DNA obtainable is on the order of several tens of bases. A second type of DNA chips is the type also called "Stanford system", in which the DNA chip is prepared by spotting preliminarily prepared DNAs on a substrate by use of split tip pins and solidifying the DNAs. This type of DNA chips are lower than the first type in the degree of integration, but has the merit that DNA fragments on the order of 1 kb can be solidified.

According to the above-mentioned conventional DNA chip technologies, however, the number of pieces of integration and the integration density of the DNA chip itself have been small. Therefore, the amount of analysis available by one run of assay has not been sufficient. Besides, it has been difficult for the user to freely set the kinds and the number of detection substances and, further, the grouping thereof on the substrate.

In addition, in the conventional DNA chips including the detection substances arrayed on the surface of a substrate having a two-dimensional extension of DNA probes varying (not adjusted) in Tm (melting temperature) or GC content, there has been the problem that there is a high possibility of giving false positive or false negative due to exposure to the same hybridization conditions and washing conditions.

Besides, an assay system for solidifying the detection substances such as DNA probes on the surface of a substrate and for spotting a sample solution containing a target substance and an analyzer also called "reader" or "scanner" for reading the results of the reactions between the detection substances and the labeled target substance have conventionally been fabricated separately and independently. Therefore, it has been impossible to carry out the bioassay process and the subsequent reading and analyzing process in a continuous-form mode. Thus, the conventional system has been very inconvenient to use.

Further, because the amount and shape of the detection substances such as DNA probes and the sample solution droplets have been nonuniform, there has been the technical problem that the accuracy of readout of fluorescence intensity is low.

Moreover, the conventional systems have been high in cost per chip and, further, cost per integration amount, and the analyzer thereof has been very expensive.

Accordingly, it is a principal object of the present invention to provide a bioassay substrate that promises a large integration amount of detection substances solidified and a free grouping of the substances and that is inexpensive, a preferable method of manufacturing the substrate, a bioassay system that makes it possible to perform bioassay efficiently and securely, and a substrate record information readout system that makes it possible to perform an assay process and a reading and analyzing process in a continuous-form mode.

DISCLOSURE OF INVENTION

In order to solve the above-mentioned problems, first, the present invention provides a "bioassay substrate" as follows. The term "bioassay" herein means biochemical analysis based on the reactions between substances.

The present invention firstly provides a bioassay substrate includes detection surfaces on which detection substances can be solidified. The detection surfaces is provided on a surface of a disk form substrate capable of reading out record information optically. The detection surfaces are provided in groove structures provided in the substrate so as to extend in radial directions as viewed on the upper side.

Here, the term "detection substances" in the present invention widely include low-molecular substances, high-molecular substances, vital substances, and the like that are solidified on the detection surfaces either directly or via a linker and that display specific coupling reactions with a target substance labeled with a fluorescent material or the like, and the term should not be construed narrowly. The "groove structures" provided in the substrate is, for example, microchannel structures or groove structure sites extending in streak forms. In the groove structure, radial partitions may be formed of pits, cellular structures, or the like. The groove structure may have a structure that is composed of a set of pits or cellular structures. The portion where the pits or cellular structures are arranged may appear substantially like a streak as viewed on the upper side. The term "groove structure" should not be construed narrowly. One field to which the bioassay substrate including the groove structures is a disk form microchannel array.

In the bioassay substrate, for example, a disk form substrate having a diameter of about 10 cm is adopted as the substrate for solidifying the detection substances thereon; therefore, the bioassay substrate is advantageous in that a multiplicity of detection surfaces for solidifying the detection substances thereon or pits, grooves, or the like including the detection surfaces can be integrated. In other words, the bioassay substrate can provide a DNA chip, a biosensor chip, or the like, which is large in integration amount of record information.

In addition, since the detection surfaces are provided in the groove structures, which are provided in the substrate radially as viewed on the upper side and at predetermined intervals so as to obviate mutual contamination, the kinds of the detection substances can be grouped on the basis of each groove structure. For example, it is possible to perform grouping of disease outbreak marker genes on the basis of each groove structure, or to perform grouping of nucleotides (detection substances) to be solidified on the basis of each groove structure based on differences in Tm or GC content. This makes it possible to vary reaction conditions such as hybridization conditions such as buffer composition, concentration, etc., washing conditions, sample solution concentration, etc. for achieving optimum reactions of the detection substances, and to thereby markedly reduce the possibility of obtaining false positive and/or false negative upon the analyzing operation.

In addition, since the groove structures in the radial direction as viewed on the upper side, namely, extending from the center side to the outer circumference side of the disk form substrate are formed on the substrate, transport of liquid by utilizing capillarity and transport of liquid by utilizing a centrifugal force generated by rotating the disk form substrate by a predetermined method can be utilized. For example, at the time of removing an excess of the target substance, which has not actively been coupled after the reaction, a washing liquid can be transported smoothly and securely into and through the groove structures (particularly, the detection surface sites therein) from the central region of the substrate.

The present invention subsequently provides a bioassay substrate including a means for providing positional information and rotational synchronism information on the above-mentioned detection surface sites. The means may be included of wobblings or address pits provided on the substrate. The term "wobbling" herein means a slight left-right meandering, relative to the center of track, of a groove (guide groove) for recording of data by the user, for preliminarily recording on the disk the information on physical addresses on the disk. Generally, FM modulation with a slight frequency deviation relative to a frequency higher than a tracking servo band is conducted, and the amplitude of a sine wave modulation signal is cut in the substrate as a radial displacement of groove.

The bioassay substrate can be preferably utilized in the case of spotting detection substance-containing solutions and a target substance-containing solution in the manner of accurately following up to predetermined detection surface sites, based on positional information and rotation period information.

The present invention further provides a bioassay substrate in which at least any one selected from the group composed of nucleotide chains, peptides, proteins, lipids, low-molecular compounds, ribosome, and other vital substances is solidified on the detection surface sites formed on the substrate.

This substrate can be widely utilized as a biosensor chip for effecting a reaction between single-chain nucleotide chains, namely, a reaction between a DNA chip double-chain nucleotide and a peptide (protein) for hybridization, an antigen-antibody reaction, or other intermolecular reactions.

Here, the term "nucleotide chain" widely includes oligonucleotides and polynucleotides containing DNA probes formed by polymerization of nucleotide, DNAs (the whole length or fragments thereof) formed by polymerization of purine nucleotide and pyrimidine, cDNAs (cDNA probes) obtained by reverse transcription, RNAs, and the like. In the case of single chain, analysis is conducted based on the hybridization reaction with the target nucleotide molecule. In the case of double chain, analysis can be applied to the reaction between protein and DNA (a specified array site); for example, the coupling between a receptor molecule such as a hormone receptor, which is a transcription factor, and a response array DNA portion or the like can be analyzed. The term "peptide" means a substance obtained by bonding of a plurality of amino acids through peptide bonds. The term "protein" means a vital high-molecular substance including as an essential component a polypeptide chain formed by linking of L-α-amino acids through peptide bonds and includes the meanings of both simple proteins and conjugated proteins. The foregoing includes DNA fragments connected with biotin, which is firmly bonded to streptoavidin, and various ligand molecules. The term "lipid" includes phospholipid membrane. In this case, the detection surface can be utilized as a membrane model. The term "low-molecular compounds" include silane coupling agents. The silane-coupling agent is a kind of crosslinking agent, which is bonded to a silicon surface or a glass surface to function as a linker for peptide, protein, and the like. The term "vital molecules" include cells and virus particles. A treatment of the detection surfaces may be appropriately selected according to the detection substances to be solidified thereon. In some cases, the detection surfaces are treated with polylysine, which is an adsorption-preventive agent.

Next, the present invention provides "a bioassay method" as follows.

The present invention provides a bioassay method wherein detection substance-containing solutions are spotted onto detection surface sites and of a bioassay substrate includes detection surfaces on which detection substances can be solidified. The detection surfaces is provided on a surface of a disk form substrate capable of reading out record information optically, and the detection surfaces is provided in groove structures provided in the substrate radially as viewed on the upper side and at predetermined intervals, by an ink jet printing process or a micromechanical spotting process, and the detection substances spotted are solidified.

This method is preferable as a method for accurately spotting droplets containing detection substance and droplets containing an array of labeled target substance in the manner of accurately following up to predetermined detection surface sites in the groove structures.

Here, the "ink jet printing process" means a process applying nozzles used in an ink jet printer, in which the detection substances are electrically jetted from a printer head onto the substrate, as in an ink jet printer, and are fixed.

The process includes a piezoelectric type ink jet process, a bubble jet process, and a supersonic jet process. The piezoelectric type ink jet process is a process in which droplets are each caused to fly by the pressure due to a displacement generated by impressing a pulse of voltage on a piezoelectric material. The bubble jet process is a process in which droplets are each caused to fly by the pressure of a bubble generated by heating a heater in a nozzle. A silicon substrate constituting the heater is embedded in the nozzle and is controlled at about 300° C./s to form a uniform bubble, by which a droplet is pushed out. However, since a liquid is exposed to a high temperature, the bubble jet process is considered to be unsuitable for vital substance specimens. The supersonic jet process is a process in which a supersonic beam is applied to a free surface of a liquid to locally exert a high pressure, thereby discharging a droplet from the location where the high pressure is exerted. This process does not require a nozzle and can form a droplet with a diameter of about 1 µm at high speed.

In the present invention, the "piezoelectric type ink jet process" can be preferably used as the "ink jet printing process". Since the size of droplets can be controlled by varying the shape of the pulse to be impressed, this process is suitable for enhancing the precision of analysis. It is possible to reduce the size of the droplet where the radius of curvature of the droplet surface is smaller, and to enlarge the size of the droplet where the radius of curvature of the droplet surface is larger. In addition, it is also possible to reduce the radius of curvature by pulling the droplet surface to the inside by varying the pulse abruptly to the negative side.

The "micromechanical spotting process" is a process in which droplets containing detection substance are spotted onto detection surface sites on the substrate by use of a printing head on which microspotting pens, capillary tubes, or pairs of tweezers are mounted.

Next, the present invention provides "a bioassay system" constituted as follows.

First, the present invention firstly provides a bioassay system, which uses a bioassay substrate including detection surfaces for enabling detection substances to be solidified thereon. The detection surfaces is provided on a surface of a disk form substrate capable of reading out record information optically, the detection surfaces is provided in groove structures provided in the substrate so as to extend radially as viewed on the upper side, and the bioassay substrate provides positional information and rotational synchronism information. The system includes at least the following means (1) to (4) and the like:

A substrate rotating means for rotatably supporting the bioassay substrate; (2) a spotting device for spotting detection substance-containing solutions and a labeled target substance-containing solution onto the detection surface sites while rotating the bioassay substrate by the substrate rotating means; (3) a focus servo mechanism for maintaining a fixed distance between the spotting device and the bioassay substrate; and (4) a tracking servo mechanism for making the spotting of the solutions follow up to the detection surface sites based on the positional information and rotational synchronism information.

In this bioassay system, the spotting distance is maintained at a fixed value with high accuracy by the focus servo mechanism while rotating the disk form bioassay substrate based on the positional information and the rotational synchronism information on the substrate, whereby droplets with uniform shape can be spotted into fixed areas in the detection surface sites provided at predetermined positions, and fluorescence intensity can be detected with good reproducibility. In addition, the tracking servo mechanism ensures that the detection substance-containing solutions and the target substance-containing solution can be securely spotted while sequentially following up to the detection surface sites in the predetermined groove structures. As a result, the reactions between the detection substances and the labeled target substance can be effected with high precision, and analytical signals can be made stable, leading to an enhanced accuracy of analysis.

Here, the spotting device, which can be preferably adopted in the bioassay system, is either an ink jet printing device or a micromechanical spotting device. The ink jet printing device means a device capable of performing the above-described "ink jet printing process", while the micromechanical spotting device means a device capable of performing the above-described "mechanical spotting process". Incidentally, in the case where the ink jet printing device is adopted, a device capable of performing the piezoelectric type ink jet printing process is preferred, for the above-mentioned ground.

Here, in a fabrication where the ink jet printing device is adopted as the spotting device in the bioassay system, ink jet nozzles are integrated to a support body disposed opposite to the bioassay substrate for containing an objective lens for emitting to the substrate a laser beam for the functions of focus servo and tracking servo.

This fabrication in which the ink jet nozzles are integral with the support body ensures that the spotting of predetermined solutions onto the substrate can be performed synchronously with the focus servo and the tracking servo, promising a compact system design.

Next, the present invention provides "a substrate record information readout system" constituted as follows.

The substrate record information readout system according to the present invention is characterized firstly in that it is unitized with the above-described bioassay system, wherein focus servo and tracking servo are applied to the bioassay substrate, the fluorescence-labeled target substance coupled with the detection substances on the detection surfaces is irradiated with a laser beam condensed by a pickup lens or the like, and the fluorochrome intensities of the fluorescence induced upon the irradiation are detected.

According to this means, the bioassay system, which is capable of effecting the reactions between substances by solidifying the detection substances such as DNA probes on the surface of the substrate and subsequently spotting thereon the target substance containing sample solution, and the readout system, which reads out the information on the reactions between the detection substances and the target substance are integrally united with each other. Therefore, the assay process and the subsequent readout process can be performed in a continuous-form mode.

Thus, the present invention has the technical significance of providing a novel technology pertaining to DNA chips and biosensor chips.

BEST MODE FOR CARRYING OUT THE INVENTION

Figure 1:
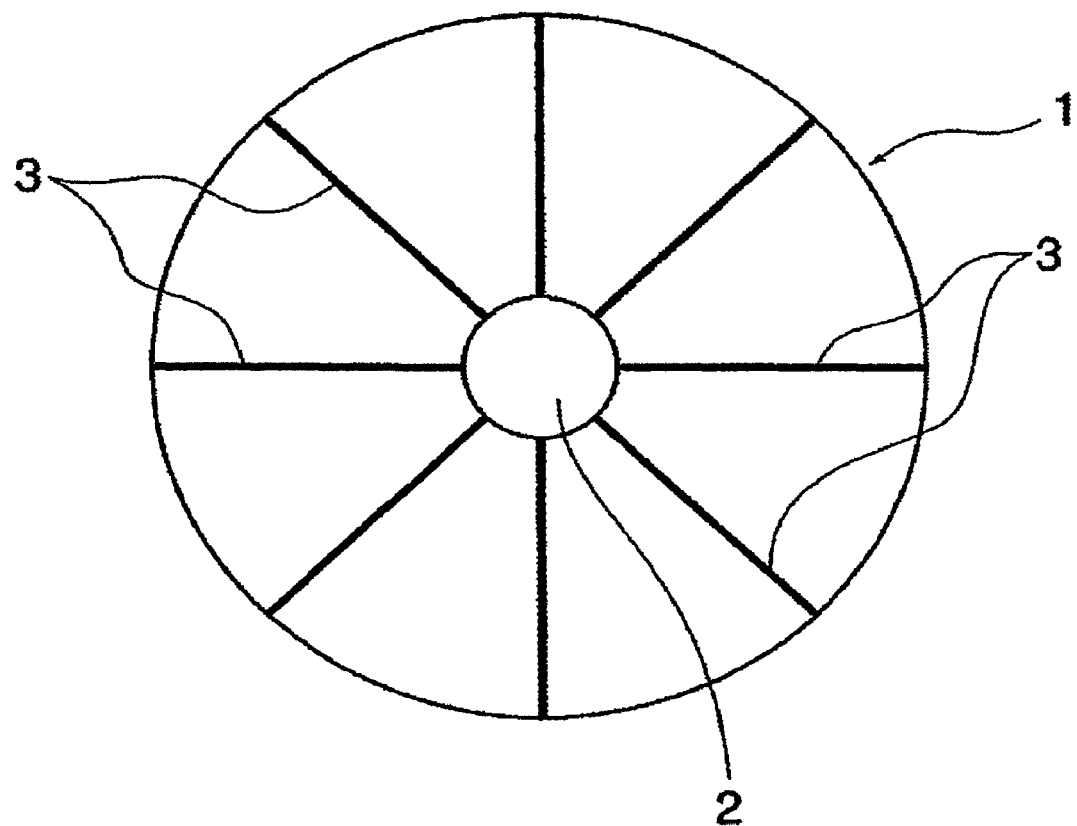
FIG. 1 shows the appearance of a bioassay substrate according to a preferred embodiment of the present invention, as viewed on the upper side.
Figure 2:
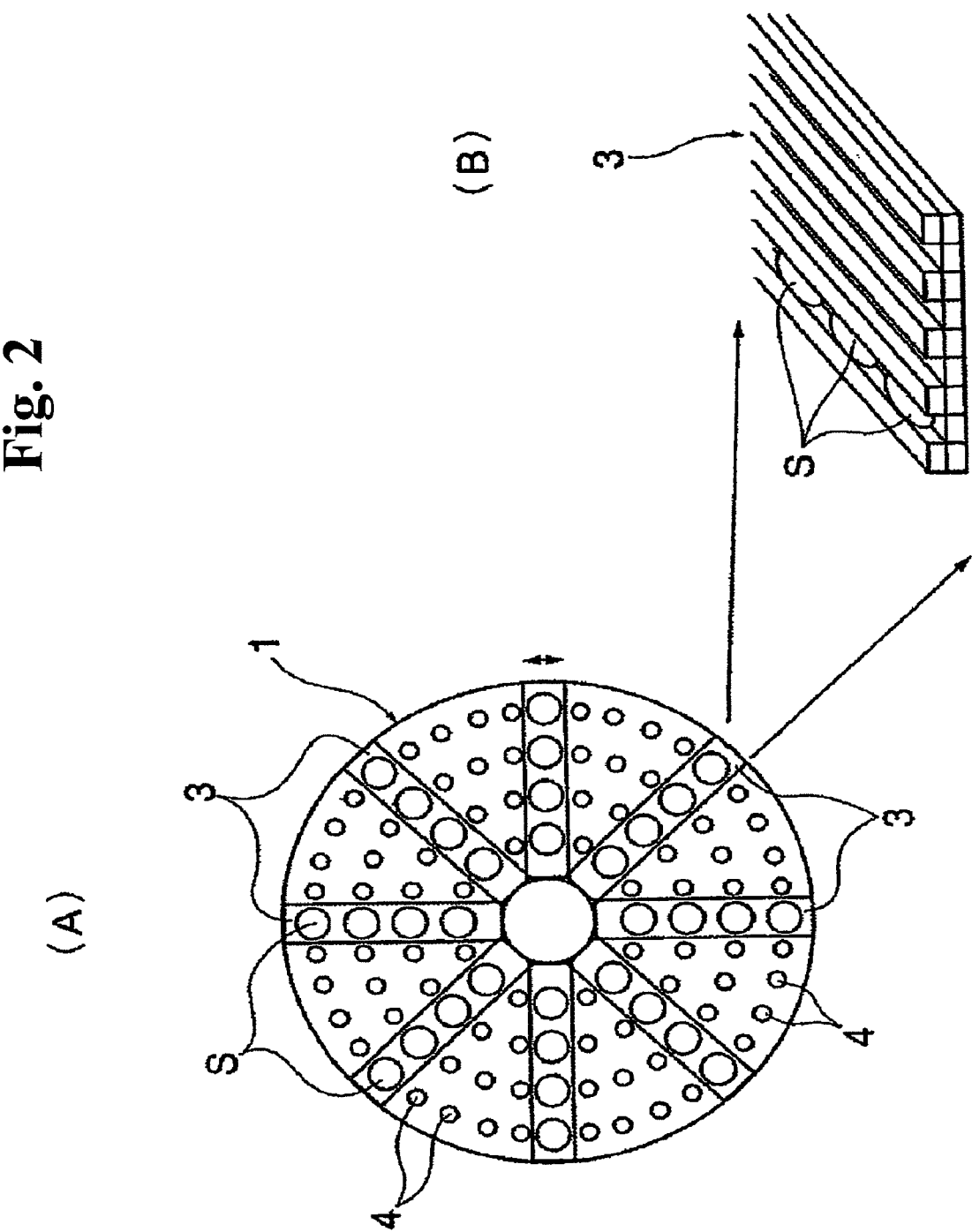
FIG. 2(A) is a schematic view showing, in a partially exaggerated manner, the constitution of the substrate.
FIG. 2(B) is a partial enlarged view showing one embodiment of the part of a groove structure (3) disposed on the substrate.

Now, preferred embodiments of the present invention will be described below referring to the accompanying drawings. FIG. 1 shows the appearance of a bioassay substrate according to a preferred embodiment of the present invention as viewed on the upper side. FIG. 2(A) is a schematic view, in a partially exaggerated manner, of the constitution of the substrate. FIG. 2(B) is a partial enlarged view showing the constitution of an embodiment of the part of a groove structure disposed on the substrate.

First, numeral 1 in FIG. 1 denotes the preferred embodiment of the bioassay substrate according to the present invention. The bioassay substrate 1 (hereinafter referred to simply as "the substrate 1") is formed of a base material adopted for a disk form substrate (disk) used for an optical information recording medium such as CD, DVD, and MD.

The base material is formed in a disk shape from quartz glass, silicon, or a synthetic resin capable of being molded into the disk shape, such as polycarbonate and polystyrene, preferably a synthetic resin capable of being injection molded. Use of an inexpensive synthetic resin substrate can promise a lower running cost, as compared with the case of a glass chip, which has been conventionally used. The substrate 1 is provided at its center with a hole 2 for fixing onto a spindle provided in a substrate rotating means, which will be described later.

On one surface of the substrate 1, a vapor-deposited aluminum layer about 40 nm in thickness is provided, which functions as a reflective film. The reflective film provides a surface reflectance of not less than 4%, from the substrate itself having a refractive index of not less than 1.5. On the upper side of the reflective film is provided a light-transmitting layer formed of transparent glass, transparent resin, or the like. Where the base material is a high reflectance material, the surface of the base material itself functions as the reflective surface. Therefore, the reflective film may be omitted. In addition, where a high reflectance film composed of a metallic film or the like is provided, the fluorescence intensity of a fluorescence-labeled target substance can be detected with better sensitivity.

The light-transmitting layer is provided with groove structures 3 extending radially (as viewed on the upper side) from the central portion of the substrate 1, at predetermined intervals. In each of the groove structures 3, detection surface sites S (see FIG. 2) surface-treated so as to enable solidification of detection substances are provided in the state of being aligned at predetermined intervals in the radial direction. The detection surface sites S may be formed at pit portions arranged in each of the groove structures 3, and may be formed over the whole range of the inside wall surface of each of the groove structures 3.

Figure 3:
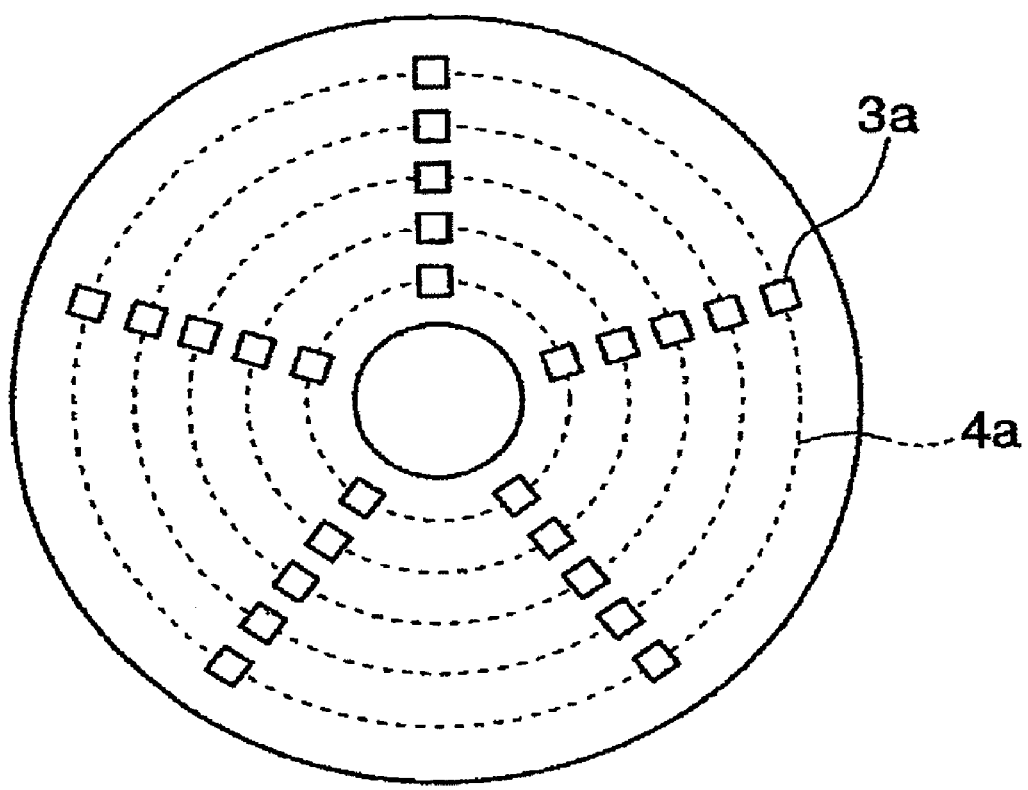
FIG. 3 shows the appearance of a modified embodiment of the substrate, as viewed on the upper side.

Besides, as shown in FIG. 3, which shows the appearance of a modified embodiment of the substrate 1, detection surface sites S may be formed in cellular pits 3a, a plurality of which are aligned in the radial direction, and a plurality of rows each composed of the radially aligned pits 3a may be provided in the circumferential directions. When droplets are spotted onto the detection surfaces provided in the groove structures 3 or the pits or cellular pits 3a in the groove structures, substantially the same spot size can be realized, so that detection of fluorescence intensity with good reproducibility can be realized. Incidentally, symbol 4a in FIG. 3 denotes address pits or the like.

The detection surface sites S have been appropriately selectively subjected to a preferable surface treatment for solidifying desired detection substances such as DNA probes. For example, the detection surface sites S are surface treated with an amino group-containing silane coupling agent solution or a polylysine solution. In the case of a synthetic resin substrate, the surface thereof is treated with plasma or by irradiation with DUV (deep UV, far ultraviolet rays), followed by the treatment with the amino group-containing silane coupling agent solution.

In addition, the detection surfaces may be plated with copper, silver, aluminum, or gold by sputtering, and the surface of the sputtered metallic film may be coated with a substance having a functional group (active group) such as amino group, thiol group, carboxyl group, etc., cysteamine, storeptoavidin, or the like. Besides, a linker or linkers for solidification of the detection substances may be bonded to the detection surfaces, as required.

The substrate 1 is preliminarily provided, along its rotational direction, with a multiplicity of address pits 4, 4 . . . formed by a optical disk mastering process. Here, positional information and rotational synchronism information will be described. Where the substrate 1 is considered as an optical disk, the groove structures 3 constituting the spotting and detecting positions are considered as user data areas, while the other areas are provided with arrays of synchronizing pits by a sample servo system or the like and are utilized also as tracking servo. Further, an address portion (geographic address on the disk) is inserted immediately on the rear side thereof, to provide the positional information.

The address portion begins with a sector mark constituting a leading pattern. The address is formed of a combination of a Variable Frequency Oscillator (VFO) for giving a rotational phase of the disk being actually rotated, an address mark for giving the start position of the address data, an identifier (ID) containing track and sector numbers, etc.

Instead of using the address pits, wobblings may be formed on the track, and the meandering of the wobblings may be so adjusted as to provide clock information according to position, in which case addressing is performed by picking up the positional information on the disk. Simultaneously, tracking servo can be performed by utilizing the frequency component of the wobblings. Furthermore, by providing the address pits and the wobblings in combination, it is possible to realize addressing and tracking servo with higher accuracy.

Next, a preferred embodiment of a bioassay system according to the present invention, which uses the above-described substrate 1, will be described based on FIG. 4, which is a block diagram briefly illustrating the constitution of the bioassay system.

Figure 4:
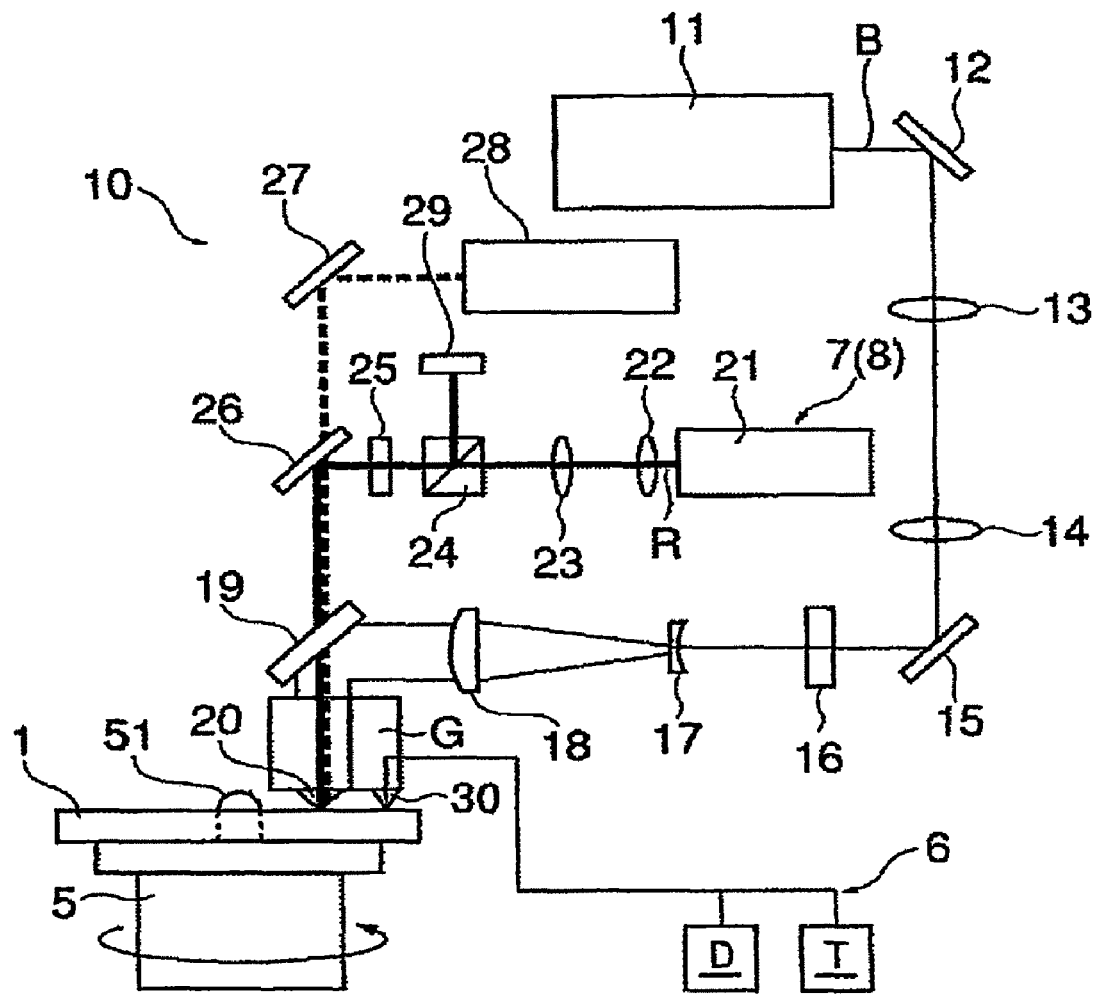
FIG. 4 is a block diagram briefly showing the constitution of a preferred embodiment of a bioassay system according to the present invention.

First, the bioassay system 10 shown in FIG. 4 is a bioassay system using the substrate 1 constituted as described above. The bioassay system 10 includes: a substrate rotating means 5 for rotatably supporting the substrate 1; a spotting device 6 for spotting detection substance-containing solutions D and a labeled target substance-containing solution T onto the detection surface sites S in a predetermined order and with predetermined timings, while rotating the substrate 1 by the substrate rotating means 5; a focus servo mechanism 7 for maintaining a fixed distance between the spotting device 6 and the substrate 1; and a tracking servo mechanism 8 for making the spotting of the solutions D and T follow up to the detection surface sites S on the substrate 1, based on the positional information and the rotational synchronism information obtained from the substrate 1.

Here, the bioassay system 10 includes a blue semiconductor laser 11 as an excitation light source. The system 10 also includes a red semiconductor laser 21 for the functions of the focus servo mechanism 7 and the tracking servo mechanism 8.

The blue semiconductor laser 11 functions as the excitation light source for reading out the reaction information from the substrate 1. First, a laser beam B emitted from the blue semiconductor laser 11 is reflected at a right angle by a reflective mirror 12. Next, the laser beam B is converted into a parallel beam by lenses 13 and 14 aligned in the propagating direction of the reflected beam.

The parallel beam is reflected at a right angle by a reflective mirror 15 and is converted into circularly polarized light beam while passing through a λ/4 plate 16. The circularly polarized light beam is enlarged in beam diameter by a concave lens 17 and a convex lens 18, is then reflected by a dichroic mirror 19, and is incident on an objective lens 20 disposed opposite to the substrate 1. Incidentally, the objective lens 20 is contained in a support body G.

The dichroic mirror 19 is so designed as to reflect the light component in a wavelength band centered on the wavelength of the laser beam B emitted from the blue semiconductor laser 11 and to transmit the other light components. To be more specific, the dichroic mirror 19 is so designed as to reflect the laser beam B and to transmit the fluorescent light coming from the fluorescent material on the substrate 1 excited by the laser beam B, which will be described later.

In this manner, the substrate 1 held on the substrate rotating means 5 at a position on the lower side of the objective lens 20 is irradiated with the blue laser beam B through the objective lens 20. The fluorescent light emitted from the fluorescent material (which is bonded, as a label, to the target substance) excited by the blue laser beam B passes through the objective lens 20, further passes through the dichroic mirrors 19 and 26, is reflected at a right angle by a reflective mirror 27, and is detected by a photomultiplier and Avalanche photodiode detector (detector) 28. Incidentally, the dichroic mirror 26 is so designed as to reflect the light component in a wavelength band centered on the wavelength of the red laser beam R, which will be described later, and to transmit the other light components inclusive of the fluorescent light.

Next, the red laser beam R emitted from the red semiconductor laser denoted by symbol 21 is utilized for focusing, namely, for the function of maintaining a fixed distance between the substrate 1 and the objective lens 20.

In addition, the red laser beam R is utilized for tracking servo, namely, for making the objective lens 20 follow up to the detection surface sites S in the groove structures 3 disposed in the substrate 1, based on the positional information and rotational synchronism information provided by the address pits 4 or/and the wobbled groove of the substrate 1. Incidentally, symbol 29 denotes a Position Sensor Detector (PSD) for adjusting the irradiation position of the red laser beam R.

Specifically, the laser beam R emitted from the red semiconductor laser 21 shown in FIG. 4 is converted into a parallel beam while passing through two lenses 22 and 23 aligned in the propagating direction of the laser beam R. The parallel beam is spectrally split by a polarized light beam splitter 24 disposed on the front side. One spectral component then passes through a λ/4 plate 25, is reflected at a right angle by the dichroic mirror 26, and is incident on the objective lens 20, whereas the other spectral component is led to the PSD 29.

While performing the focusing servo and the tracking servo by use of the red laser beam R emitted through the objective lens 20 as described above, to thereby read accurately the positions of the predetermined detection surface sites S of the substrate 1, the detection substance-containing solutions D or the labeled target substance-containing solution T is sequentially and accurately spotted onto the detection surface sites S with predetermined timings through ink jet nozzles 30 (hereinafter referred to simply as "nozzles 30") provided in, the support body G integrally with the objective lens 20.

Figure 5:
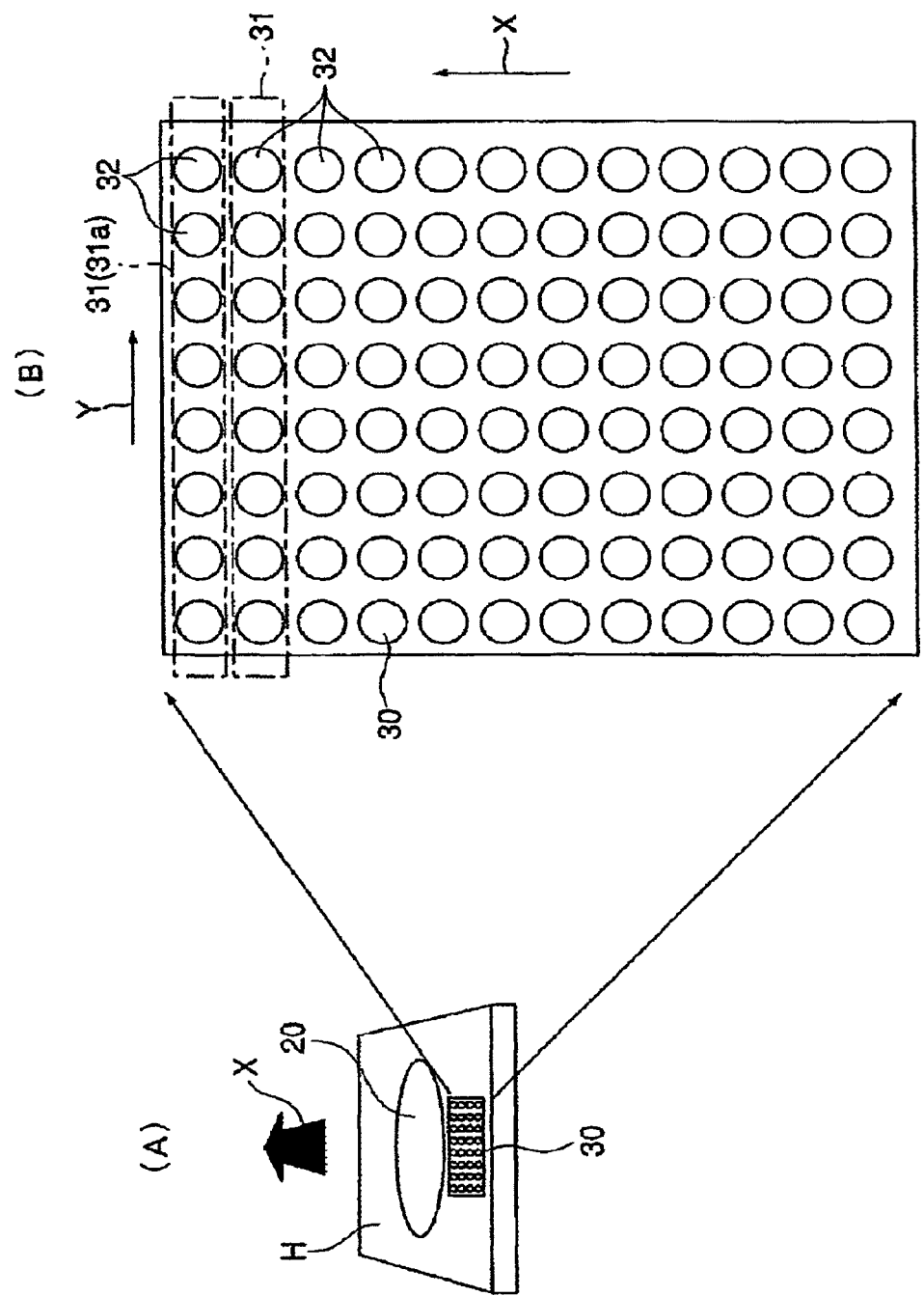
FIG. 5(A) is a perspective view of the surroundings of nozzles.
FIG. 5(B) is an enlarged plan view of the nozzles.

Next, the constitution of the nozzles 30 integrated with the objective lens 20 in the support body G will be described, based on FIGS. 5(A) and 5(B). FIG. 5(A) is a perspective view of the surroundings of the nozzles 30. FIG. 5(B) is an enlarged view of the nozzles 30.

The objective lens 20 is provided in the center of a rectangular actuator holder H for supporting the objective lens 20, and the nozzle 30 is provided in a region of the holder H on the rear side of the objective lens 20. Incidentally, a plurality of the nozzles 30 may be provided.

In addition, as the nozzles 30, piezoelectric type ink jet nozzles are preferably adopted since they have the merit that it is easy to control the size of the droplets jetted, by varying the shape of the pulse impressed on the piezoelectric material. Incidentally, the arrow X in FIGS. 5(A) and 5(B) indicates the moving direction (rotational direction) of the substrate 1.

Here, the nozzles 30 are composed of a plurality of nozzle groups 31 each of which constitutes a row of the nozzles 30 aligned in the radial direction Y and which are arrayed in the direction of arrow X. The nozzle group 31 is a set of nozzle holes 32, 32 . . . for simultaneously spotting the same detection substance-containing solution D. From the nozzle groups 31, 31 . . . , different kinds of detection substance-containing solutions D are sequentially spotted onto the corresponding detection surface sites S in the groove structures 3 of the substrate 1 on the lower side, simultaneously on the basis of each kind; subsequently, after a predetermined lapse of time, different kinds of or the same kind of labeled target substance-containing solution T is spotted onto the detection surface sites S simultaneously.

Incidentally, the period of time T after the detection substance-containing solution D is spotted onto the detection surface site S until the labeled target substance-containing solution is spotted thereon can be computed by the following formula:

$$T = [L_0 + (n-1)L_1 + 0.5\phi] \div V_1 - W/V_2$$

where $L_0$ represents the distance from the center of the objective lens to the nozzle group 31a in the first row, $L_1$ represents the interval between the nozzle groups 31, $\phi$ represents the diameter of the droplets of the probe DNAs, $V_1$ represents the linear velocity of the substrate 1, W represents the distance from the nozzles 30 to the substrate 1, and $V_2$ represents the velocity of the droplets jetted from the nozzles 30. According to the above formula, the target substance-containing solution can be spotted right onto the droplet of the detection substance-containing solution.

Finally, a bioassay process, which can be carried out by use of the substrate 1, will be briefly described based on FIGS. 6(A) to 6(E), which illustrate the flow of the bioassay process that can be carried out using the substrate 1.

First, the hole 2 of the substrate 1 is fixed to the spindle 51 (see FIG. 4) of the substrate rotating means 5 (see FIG. 4), and the substrate 1 is rotated. While detecting the positional information by the focus servo mechanism 7 or/and the tracking servo mechanism 8, the detection substance-containing solutions $D_1$, $D_2$ . . . are spotted from the nozzles 30 (nozzle groups 31) disposed opposite to the substrate 1 onto the predetermined detection surface sites S (see FIG. 2) provided on the substrate 1, based on the ink jet printing process (see FIG. 6(A)).

Subsequently, while detecting the positional information by the focus servo mechanism 7 or/and the tracking servo mechanism 8 (see FIG. 4), the fluorescence-labeled target substance-containing solution T is spotted from the nozzles 30 (nozzle groups 31) disposed opposite to the substrate 1 onto the detection surface sites S by the ink jet printing process (see FIG. 6(B)).

Figure 6:
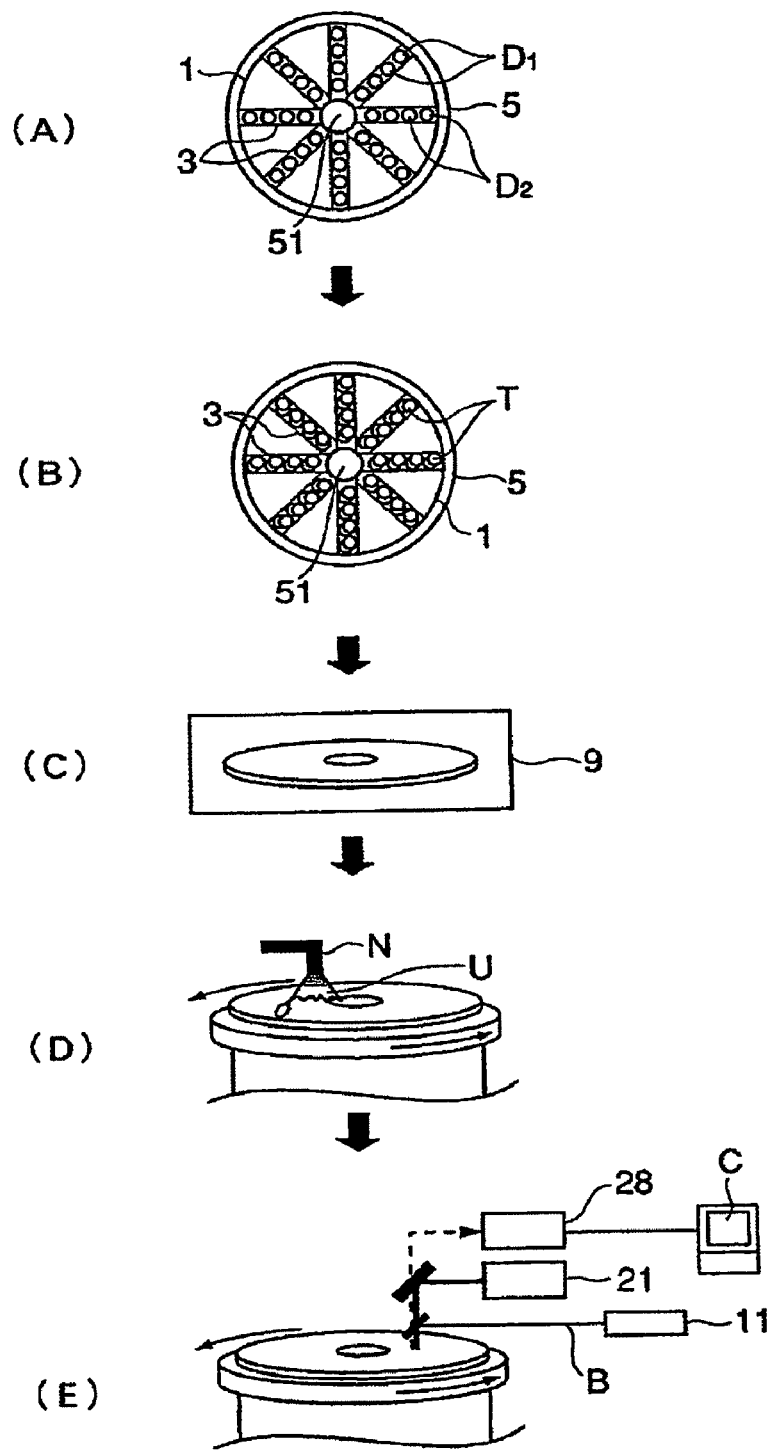
FIGS. 6(A) to 6(E) illustrate the flow of a bioassay process, which can be carried out by use of the bioassay substrate.

Next, for optimally effecting coupling reactions such as hybridization between the detection substances and the labeled target substance in the detection surface sites S on the substrate 1, the substrate 1 is warmed for several hours in a thermohygrostat 9 (see FIG. 6(C)).

Subsequently, while again rotating the substrate 1 by the spindle 51, a predetermined washing liquid U is dripped from a washing nozzle N disposed opposite to the substrate 1, to remove from the detection surface sites S the labeled target substance that has not undergone the active coupling reaction. As the washing liquid, for example, a Saline-Sodium Citrate (SSC) buffer solution containing a surfactant SDS is used (see FIG. 6(D)).

The substrate 1 is irradiated with the blue laser beam B to excite each of the detection surface sites S, the magnitude of fluorescence intensity is detected by the detector 28, and the results of the coupling reactions between the detection substances and the labeled target substance are judged. Finally, the fluorescence intensities for the individual detection surface sites S are subjected to A/D conversion, and the coupling reaction proportions are visualized by displaying the distribution thereof on the screen of a computer C (see FIG. 6(E)).

EXAMPLE

A quartz glass substrate 12 cm in diameter was used. In the surface area of the substrate ranging from a radius of 20 mm to a radius of 40 mm, a groove with a track pitch of 50 μm, a duty of 70%, and a groove depth of 500 nm was formed by etching. The substrate surface was spin coated with a 0.3 wt % ethanol solution of a silane-coupling agent (product code: A1100, a product by Nippon Unitika K.K.), followed by drying in a bake furnace at 100° C. for 2 hours.

Further, the silane-treated substrate surface was spin-coated with a solution prepared by dissolving photobiotin (N-(4-azido-2-nitrophenyl)-N'-(3-biotinylaminopropyl)-N'-methyl-1,3-propanydiamine (acetate); a product by Sigma-Aldrich) in distilled water in a concentration of 10 μg/ml.

By using a red semiconductor laser for emitting a red laser beam with a wavelength of 680 nm and condensing the laser beam by a pickup lens with an NA of 0.45, focus servo and tracking servo were applied to the substrate. The photobiotin was irradiated with a blue laser beam from a blue semiconductor laser through an objective lens having an NA of 0.45 with modulation under the conditions of a wavelength of 405 nm, a power of 1 mW, and a frequency of 10 kHz, while maintaining a fixed distance between the substrate and the lens and in the manner of following up to the groove at a linear velocity of 1 m/s. Thereafter, the substrate thus treated was washed with distilled water, whereby photobiotin patterns were formed only in the irradiated areas, to obtain a negative type lithography.

A 25 μg/ml PBS solution of avidin (Avidin D; a product by Vector Lab) was jetted from ink jet nozzles, to be spotted onto the photobiotin patterns while applying tracking servo and focus servo, in the area in terms of r=20-30.

Next, a 250 μg/ml PBS solution of Avidin D was spotted onto the area in terms of r=30-40. Thereafter, spin-coat washing was conducted by use of a phosphate buffer solution (product code: 1003; a product by Sugma).

While again applying tracking servo and focus servo to the substrate by use of a red laser beam with a wavelength of 680 nm from the red semiconductor laser, to follow up to the groove, a blue laser beam with an output of 100 μW and a beam diameter of 2 mm was emitted from a blue semiconductor laser, the substrate was irradiated with the laser beam through the objective lens with an NA of 0.45 at a linear velocity of 5 m/s, and fluorescence intensities were read out.

As the detector, a photomultiplier (product code: H5784-01; a product by Hamamatsu Photonics K.K.) was used. The time required for readout was about 6.3 sec for r=20-30, and about 8.8 sec for r=20-40. It was thus found out that the reading process can be carried out in a very short time, as compared with a conventional reading system.

The fluorescence intensity was 120 mV on average for the 25 μg/ml solution, and 600 mV on average for the 250 μg/ml solution, with a fluorescence intensity ratio of 1/5. The scattering of fluorescence intensity was σ=1 mV for both the solutions; thus, a very high accuracy of analysis was obtained.

(1) The bioassay substrate according to the present invention includes the detection surface sites arrayed in the groove structures disposed radially as viewed on the upper side. Therefore, a large amount of and a large number of detection substances can be integrated thereon. In addition, since assay can be carried out by arranging a plurality of detection substances in a grouped pattern and selecting the optimal reaction conditions and the like on the basis of each groove structure, the rate of generation of false positive and false negative results is markedly reduced. Therefore, according to the bioassay substrate, a comprehensive and efficient analysis can be performed with high accuracy. Besides, cost per bit of record information is also low.

(2) The bioassay substrate according to the present invention is particularly useful as a DNA chip and a biosensor chip. In addition, it can provide a disk form microchannel array having a novel structure. Where the substrate is utilized as a DNA chip, it can be utilized for gene mutation analysis, SNPs (monobasic polymorphism) analysis, gene expression frequency analysis, etc., and can be used to utmost in a wide range of fields including novel medicament development, clinical diagnosis, pharmacogenomics, and forensic medicine. Where the substrate is utilized as a biosensor chip, it can be utilized for examination of antigen-antibody reactions, calibration of incretion disturbing substances, etc.

(3) Next, the bioassay system according to the present invention can smoothly perform the process of spotting and solidifying detection substances on the substrate, and the subsequent series of processes of spotting a labeled target substance, reaction, washing, and readout and analysis of the reaction results, to make it possible to perform the process from assay to analysis efficiently, speedily, and highly conveniently.

(4) By use of the substrate information readout system unitized with the assay system according to the present invention, it is possible to perform in a continuous-form mode the complicated operations of periodically spotting detection substance-containing solutions onto the substrate while applying focus servo and/or tracking servo to the substrate, then solidifying the detection substances such as DNA probes, antibodies, etc. on predetermined detection surfaces, further spotting a fluorescence-labeled target substance such as cDNA, antigen, etc. on the detection surface sites while again applying the focus servo and/or tracking servo, then performing a predetermined reaction promoting process, washing the substrate under predetermined conditions, and finally exciting the fluorescent material by a laser beam to detect the fluorescent emission amounts to read out information on the reaction results.

The invention claimed is:

1. A bioassay system using a bioassay substrate comprising detection surfaces on which detection substances can be solidified, said detection surfaces being provided on a surface of a disk form substrate capable of reading out record information optically, said detection surfaces being provided in groove structures provided in said surface of said substrate, wherein said groove structures comprise a plurality of grooves that extend in radial directions as viewed on an upper side, wherein said grooves extend continuously from a hole at a center of said disk to an outer circumference of said disk such that each of the plurality of grooves forms a fluidically continuous flow path, and said bioassay substrate providing positional information and rotational synchronism information, wherein said bioassay system comprises, at least:
   substrate rotating means for rotatably supporting said bioassay substrate;
   a spotting device for spotting detection substance-containing solutions and a labeled target substance-containing solution onto said detection surface sites, while rotating said bioassay substrate by said substrate rotating means;
   a focus servo mechanism for maintaining a fixed distance between said spotting device and said bioassay substrate; and
   a tracking servo mechanism for making said spotting of said solutions follow up to said detection surface sites, based on said positional information and said rotational synchronism information.

2. The bioassay system as set forth in claim 1, wherein said spotting device is at least one selected from the group composed of an ink jet printing device and a micromechanical spotting device.

3. The bioassay system as set forth in claim 1, wherein said spotting device is an ink jet printing device, and ink jet nozzles are integrated to a support body disposed opposite to said bioassay substrate for containing an objective lens for emitting to said bioassay substrate a laser beam for the functions of focus servo and tracking servo.

4. The readout system unitized with a bioassay system as set forth in claim 1, for reading out record information on said bioassay substrate, wherein focus servo and tracking servo are applied to said bioassay substrate, a fluorescence-labeled target substance coupled with said detection substances on said detection surfaces is irradiated with a condensed laser beam, and fluorochrome intensities of fluorescence induced by excitation upon said irradiation are detected.

5. The bioassay system as set forth in claim 1, wherein said groove structures are disposed at even intervals around said hole of said disk.

6. The bioassay system as set forth in claim 1, wherein said detection surfaces comprises a surface treatment configured to solidify said detection substances.

7. A bioassay system using a bioassay substrate comprising detection surfaces on which detection substances can be solidified, the detection surfaces being provided on a surface of a disk form substrate capable of reading out record information optically, the detection surfaces being provided at pit portions within groove structures provided in the surface of the substrate, wherein the groove structures comprise a plurality of grooves that extend in radial directions as viewed on an upper side, wherein the grooves extend continuously from a hole at a center of the disk to an outer circumference of the disk such that each of the plurality of grooves forms a fluidically continuous flow path, and the bioassay substrate providing positional information and rotational synchronism information, wherein the bioassay system comprises, at least:
   a substrate rotating unit for rotatably supporting the bioassay substrate;
   a spotting device for spotting detection substance-containing solutions and a labeled target substance-containing solution onto the detection surface sites, while rotating the bioassay substrate by the substrate rotating unit;
   a focus servo mechanism for maintaining a fixed distance between the spotting device and the bioassay substrate; and
   a tracking servo mechanism for making the spotting of the solutions follow up to the detection surface sites, based on the positional information and the rotational synchronism information.

8. The bioassay system as set forth in claim 7, wherein the pit portions are formed at predetermined intervals within the groove structures.

9. The bioassay system as set forth in claim 7, wherein address pits are formed on the surface of the disk form substrate between the groove structures, wherein a plurality of the address pits are formed at a radial distance from the hole equal to a radial distance from the hole at which a plurality of the detection surfaces are provided.

10. The bioassay system as set forth in claim 7, wherein the spotting device is at least one selected from the group composed of an ink jet printing device and a micromechanical spotting device.

11. The bioassay system as set forth in claim 7, wherein the spotting device is an ink jet printing device, and ink jet nozzles are integrated to a support body disposed opposite to the bioassay substrate for containing an objective lens for emitting to the bioassay substrate a laser beam for the functions of focus servo and tracking servo.

12. The readout system unitized with a bioassay system as set forth in claim 7, for reading out record information on the bioassay substrate, wherein focus servo and tracking servo are applied to the bioassay substrate, a fluorescence-labeled target substance coupled with the detection substances on the detection surfaces is irradiated with a condensed laser beam, and fluorochrome intensities of fluorescence induced by excitation upon the irradiation are detected.

* * * * *